US009237866B2

(12) United States Patent
Christensen et al.

(10) Patent No.: US 9,237,866 B2
(45) Date of Patent: Jan. 19, 2016

(54) BLOOD GLUCOSE MANAGEMENT

(71) Applicant: Birch Narrows Development LLC, Stillwater, MN (US)

(72) Inventors: Curtis Christensen, Stillwater, MN (US); Daniel Davis, Hugo, MN (US); Erik Davis, St Louis Park, MN (US)

(73) Assignee: Birch Narrows Development, LLC, Stillwater, MN (US)

( * ) Notice: Subject to any disclaimer, the term of this patent is extended or adjusted under 35 U.S.C. 154(b) by 80 days.

(21) Appl. No.: 13/946,838

(22) Filed: Jul. 19, 2013

(65) Prior Publication Data

US 2014/0323915 A1     Oct. 30, 2014

Related U.S. Application Data

(60) Provisional application No. 61/817,172, filed on Apr. 29, 2013.

(51) Int. Cl.
*A61B 5/151* (2006.01)
*A61B 5/15* (2006.01)

(52) U.S. Cl.
CPC ............ *A61B 5/15101* (2013.01); *A61B 5/1411* (2013.01); *A61B 5/15105* (2013.01);
(Continued)

(58) Field of Classification Search
CPC ................... A61B 5/150969; A61B 5/15105; A61B 5/15142; A61B 2562/0295; G01N 33/4875
USPC .......... 600/300, 347, 583, 584; 436/808, 811, 436/63, 95; 606/181, 182, 167; 422/547, 422/551, 552, 559; 435/4, 14; 204/400, 204/406, 407, 403.01, 403.02, 403.03
See application file for complete search history.

(56) References Cited

U.S. PATENT DOCUMENTS

| 4,648,408 A | 3/1987 | Hutcheson et al. |
| 5,014,718 A | 5/1991 | Mitchen |

(Continued)

FOREIGN PATENT DOCUMENTS

| WO | 9309710 A1 | 5/1993 |
| WO | 2005000118 A1 | 1/2005 |
| WO | WO 2012119128 A1 * | 9/2012 |

OTHER PUBLICATIONS

International Searching Authority, "Invitation to Pay Additional Fees and, Where Applicable, Protest Fee", Jul. 10, 2014, 6 pages, Rijswijk, The Netherlands.

(Continued)

*Primary Examiner* — Devin Henson
*Assistant Examiner* — David J McCrosky
(74) *Attorney, Agent, or Firm* — Fredrikson & Byron, P.A.

(57) ABSTRACT

This disclosure provides equipment and processes for blood glucose management. Embodiments may comprise a lancet device that includes a base that supports a lancet and a cover. The cover can move controllably from an un-depressed position to a depressed position when a predetermined force is applied. The cover can provide access to the lancet in the depressed position. In another aspect, a biological test kit may include a reusable module and a disposable module. The disposable module may include one or more lancet devices such as that described above to collect a biological sample, one or more strip stations supporting biological strips and a disposable module connector. The reusable module may support measuring equipment to measure a property of the biological sample and a reusable module connector that engages removably with the disposable module connector.

13 Claims, 9 Drawing Sheets

(52) U.S. Cl.
CPC ....... *A61B5/15142* (2013.01); *A61B 5/150969* (2013.01); *A61B 5/15019* (2013.01); *A61B 5/150022* (2013.01); *A61B 5/15144* (2013.01); *A61B 5/150213* (2013.01); *A61B 5/150412* (2013.01); *A61B 5/150503* (2013.01); *A61B 5/150633* (2013.01); *A61B 5/150664* (2013.01)

(56) References Cited

U.S. PATENT DOCUMENTS

| | | | |
|---|---|---|---|
| 5,054,499 | A | 10/1991 | Swierczek |
| 5,070,886 | A | 12/1991 | Mitchen et al. |
| 5,139,029 | A | 8/1992 | Fishman et al. |
| 5,201,324 | A | 4/1993 | Swierczek |
| 5,231,993 | A | 8/1993 | Haber |
| 5,304,192 | A | 4/1994 | Crouse et al. |
| 5,324,303 | A | 6/1994 | Strong et al. |
| 5,402,798 | A | 4/1995 | Swierczek et al. |
| 5,505,212 | A | 4/1996 | Keljmann et al. |
| 5,529,581 | A | 6/1996 | Cusack |
| 5,540,709 | A | 7/1996 | Ramel |
| 5,624,458 | A | 4/1997 | Lipscher |
| 5,630,828 | A | 5/1997 | Mawhirt et al. |
| 5,636,640 | A | 6/1997 | Staehlin |
| 5,709,699 | A | 1/1998 | Warner |
| 5,807,375 | A | 9/1998 | Gross et al. |
| 5,971,941 | A | 10/1999 | Simons et al. |
| 6,036,924 | A | 3/2000 | Simons et al. |
| 6,071,294 | A | 6/2000 | Simons et al. |
| 6,132,449 | A | 10/2000 | Lum et al. |
| 6,228,100 | B1 | 5/2001 | Schraga |
| 6,299,626 | B1 | 10/2001 | Viranyi |
| 6,302,855 | B1* | 10/2001 | Lav et al. ............. 600/584 |
| 6,364,890 | B1 | 4/2002 | Lum et al. |
| 6,472,220 | B1 | 10/2002 | Simons et al. |
| 6,553,244 | B2* | 4/2003 | Lesho et al. ............. 600/347 |
| 6,562,014 | B2 | 5/2003 | Lin et al. |
| 6,591,124 | B2 | 7/2003 | Sherman et al. |
| 6,679,852 | B1 | 1/2004 | Schmelzeisen-Redeker et al. |
| 6,706,159 | B2 | 3/2004 | Moerman et al. |
| 7,001,344 | B2 | 2/2006 | Freeman et al. |
| 7,150,755 | B2 | 12/2006 | Levaughn et al. |
| 7,291,159 | B2 | 11/2007 | Schmelzeisen-Redeker et al. |
| 7,374,949 | B2 | 5/2008 | Kuriger |
| 7,378,007 | B2 | 5/2008 | Moerman et al. |
| 7,537,571 | B2 | 5/2009 | Freeman et al. |
| 7,544,185 | B2 | 6/2009 | Bengtsson |
| 7,666,149 | B2 | 2/2010 | Simons et al. |
| 7,771,367 | B2 | 8/2010 | Haar et al. |
| 7,846,110 | B2 | 12/2010 | Kloepfer et al. |
| 7,959,581 | B2 | 6/2011 | Calasso et al. |
| 8,142,465 | B2 | 3/2012 | Jankowski et al. |
| 8,172,867 | B2 | 5/2012 | Nicholls |
| 8,211,036 | B2 | 7/2012 | Schraga |
| 8,211,038 | B2 | 7/2012 | Wang et al. |
| 8,221,332 | B2 | 7/2012 | Robbins et al. |
| 8,333,712 | B2 | 12/2012 | Imamura et al. |
| 8,961,901 | B2 | 2/2015 | Glauser et al. |
| 2002/0087180 | A1 | 7/2002 | Searle et al. |
| 2003/0050573 | A1 | 3/2003 | Kuhr et al. |
| 2003/0088191 | A1 | 5/2003 | Freeman et al. |
| 2003/0153939 | A1 | 8/2003 | Fritz et al. |
| 2003/0191415 | A1 | 10/2003 | Moerman et al. |
| 2005/0085840 | A1 | 4/2005 | Yi et al. |
| 2005/0234491 | A1 | 10/2005 | Allen |
| 2005/0245844 | A1 | 11/2005 | Mace et al. |
| 2006/0058827 | A1 | 3/2006 | Sakata |
| 2006/0184189 | A1 | 8/2006 | Olson et al. |
| 2006/0271084 | A1 | 11/2006 | Schraga |
| 2007/0088377 | A1 | 4/2007 | LeVaughn et al. |
| 2007/0112281 | A1 | 5/2007 | Olson |
| 2007/0129620 | A1 | 6/2007 | Krulevitch et al. |
| 2007/0293882 | A1 | 12/2007 | Harttig et al. |
| 2008/0058726 | A1 | 3/2008 | Jina et al. |
| 2009/0099427 | A1 | 4/2009 | Jina et al. |
| 2009/0204027 | A1 | 8/2009 | Zuk et al. |
| 2009/0259146 | A1 | 10/2009 | Freeman et al. |
| 2009/0299397 | A1 | 12/2009 | Ruan et al. |
| 2010/0023045 | A1 | 1/2010 | Macho et al. |
| 2010/0292609 | A1 | 11/2010 | Zimmer et al. |
| 2011/0040317 | A1 | 2/2011 | Lee et al. |
| 2011/0137203 | A1 | 6/2011 | Nishiuchi et al. |
| 2011/0238101 | A1 | 9/2011 | Nishiuchi |
| 2011/0270129 | A1 | 11/2011 | Hoerauf |
| 2012/0123297 | A1 | 5/2012 | Brancazio |
| 2012/0203083 | A1 | 8/2012 | Christensen et al. |
| 2012/0226123 | A1 | 9/2012 | Schiff et al. |
| 2012/0302919 | A1 | 11/2012 | Robbins et al. |
| 2014/0011288 | A1 | 1/2014 | Krämer et al. |
| 2014/0170761 | A1* | 6/2014 | Crawford et al. ............. 436/95 |

OTHER PUBLICATIONS

International Searching Authority, "Notification of Transmittal International Search Report and the written Opinion of the International Searching Authority", Sep. 19, 2014, 17 pages, Rijswijk, The Netherlands.

International Preliminary Report on Patentability mailed on Apr. 1, 2015, in PCT Application PCT/US2014/035507 filed Apr. 25, 2014, 21 pages.

* cited by examiner

BLOOD GLUCOSE MANAGEMENT

RELATED APPLICATION

This application claims priority to provisional application U.S. Ser. No. 61/817,172 filed Apr. 29, 2013, the disclosure of which is hereby incorporated by reference herein in its entirety.

TECHNICAL FIELD

This disclosure relates to technology for collecting biological samples to measure a biological property.

BACKGROUND

Monitoring blood glucose several times per day is a recommended way for controlling blood glucose levels in patients managing diabetes. Good blood glucose control minimizes loss of life, reduces limb amputations, and enhances quality of life for hundreds of millions of people. It is often recommended by physicians that patients managing diabetes monitor blood glucose levels typically four times a day to mitigate the risks of poor blood glucose control.

Devices for managing blood glucose typically include a lancing tool. In operation, the tool is opened, and a disposable lancet can be uncovered and inserted into the tool. The user can position the tip against his or her finger and actuate the tool. After that, the blood sample can be transported to a glucose measuring device for analysis. After the lancing event is complete, standard practice is for the user to re-open the tool, and remove and dispose of the lancet. The devices may offer additional features such as a means for the user to enter a depth of insertion of the tool via a dial or a similar input mechanism.

Blood flow and pain while lancing can be adjusted by the depth of insertion of the lancet. A lancet that is inserted deeper than levels recommended for a specific user can cause a high volume of blood flow and significant pain. By contrast, a lancet that is inserted less deep than recommended levels introduces less pain, but does not draw sufficient quantity of blood for testing blood glucose levels. The lancet can also be replaced with each use to prevent risk of infection. Replacing a lancet with each use can also prevent the lancet from becoming duller with use, and consequently provide less pain while lancing. Pain, expense, and user-unfriendliness are common reasons why diabetes patients may be less likely to monitor their blood glucose levels with diligence.

SUMMARY

In one aspect, this disclosure teaches an easy-to-use lancet device that produces a sufficient amount of blood without causing undue pain so that patients are more likely to monitor biological properties for disease management. A lancet device can include a base that includes a support surface, a lancet and a cover. The cover can include a peripheral edge along which the cover is connected to the base, a cover region, a lancet aperture, and a peripheral hinge near the peripheral edge. The cover region can cover the lancet when the cover is in an un-depressed position. The lancet can be configured to protrude through the lancet aperture when the cover is in a depressed position. The peripheral hinge can facilitate controlled movement of the cover from the un-depressed position to the depressed position upon application of a predetermined depression force.

A method of collecting a biological sample may include providing a lancet device such as that discussed above. A predetermined force can be applied on the cover region. The cover can move from an un-depressed position in which the cover region covers the lancet to a depressed position in which the lancet protrudes through the lancet aperture and exposes biological fluid. A quantity of the biological fluid as the biological sample can be collected.

Certain lancet devices in accordance with embodiments of the present invention may have one or more advantages. For example, the lancet device can be easy to use because it eliminates assembly of multiple pieces. The lancet device can controllably move the skin surface onto and off of a lancet to minimize pain and maximize blood flow. In some instances, different lancet devices can be offered for users with different anatomical features—e.g., one lancet device for users with relatively thick finger skin, and another lancet device for users with relatively thin finger skin. Some embodiments with multiple lancet stations provide visual evidence of which lancet stations have been used and which ones have not yet been used. Some embodiments prevent a lancet station from being used more than once. Some embodiments provide feedback (e.g., audible and/or tactile) as lancing occurs to increase patient comfort. The lancet device can provide increased compliance because of its small size, portability and less pain during use, fewer complications during collection of the biological sample and decreased total cost.

In another aspect, this disclosure teaches a compact biological test kit for measuring a property of a biological sample that enables re-use of reusable components and disposal of disposable components. The biological test kit can include a reusable module and a disposable module. The disposable module can include one or more lancet devices, such as those described elsewhere herein, and one or more strip stations. The strip station can support one or more biological test strips that can interact with the collected biological sample. The reusable module can support measuring equipment that can measure a property of the biological sample. A reusable module connector and a disposable module connector may removably connect the reusable module and the disposable module. A display monitor can be included with the reusable module to display the measured property.

Certain biological test kits in accordance with embodiments of the present invention may have one or more advantages. For example, the biological test kit can offer ease of use and portability. In some embodiments, different components can be replaced at different intervals. For example, in embodiments with a reusable module and a disposable module, the disposable module may be replaced with each use (or after a relatively small number of uses), while the reusable module may be replaced at significantly longer intervals. In embodiments in which the disposable module is made up of a lancet station module and a strip station module, the lancet station module and the strip station module can be replaced at different intervals. Multiple lancing events can be performed with the same device, enabling a user to monitor blood glucose levels at a recommended interval. The biological test kit can enable one finger operation. In some embodiments, the entire biological test kit can be roughly the size of a credit card, which can make it more accessible, portable, increase testing compliance and enable a connected real-time management of glucose.

The details of one or more examples are set forth in the accompanying drawings and the description below. Other features, objects, and advantages will be apparent from the description and drawings, and from the claims.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
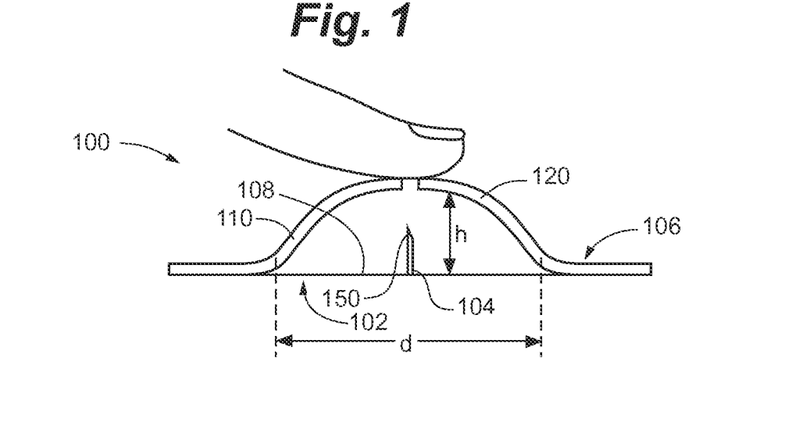
FIG. 1 is a front elevation view of a lancet device according to embodiments of the invention with the cover in an un-depressed position.

Embodiments of the invention include a lancet device 100 to collect biological samples. The lancet device 100 can include a base 102, a lancet 104, and a cover 106. The base 102 can include a support surface 108. The base 102 can be made of a material that is rigid in comparison to the cover 106. The base 102 can be made of materials such as a rigid polymer, metal, etc. The base 102 can be of any desired size or shape. The base 102 may be operably coupled to the cover 106. The support surface 108 may be a generally planar surface that can house the lancet 104. The support surface 108 in the illustrated embodiment is an upper surface of the base 102. The support surface 108 can be made of similar materials as the base 102 and can be rigid in comparison to the cover 106.

The base 102 can support a lancet 104, which can extend away from the support surface 108 at an angle of approximately 90°. In many embodiments, the lancet 104 can remain stationary with respect to the base 102. The lancet 104 can include a lancing edge 150 adapted to make an incision or a puncture on a surface (e.g., skin). The lancet 104 can be made of materials such as stainless steel or similar alloys. The lancing edge 150 can be fabricated by grinding or a similar machining technique so that the lancing edge is of a specific geometry and sharpness to pierce a surface such as skin without causing the lancet 104 to break. The lancet 104 can be configured to pierce the skin of a user to collect a quantity of blood sample.

The cover 106 can be operably coupled to the base 102 of the lancet device 100. The cover 106 can include a peripheral edge 110 along which the cover is connected to the base. In some embodiments, the cover 106 can be coupled to the base 102 at a selected location near the peripheral edge 110. In some embodiments, the cover 106 can be coupled to the base 102 along the entire peripheral edge 110. The cover 106 can be made of a polymeric material that has a sufficiently large elasticity to move a specific distance when a specified force is applied on the cover. The polymeric or metallic material may be selected to include favorable elastic properties that allow the cover to move in a controlled manner. Instead of or in addition to engineered polymers, a spring, foam, cam and helix device, or other suitable mechanism can be included between the cover 106 and the base 102 that facilitates controlled movement of the cover when a predetermined depression force is applied.

The cover 106 can include a cover region 120 configured to cover the lancet 104 when the cover 106 is in an un-depressed position. The cover region 120 has a hemispherical or domed shape in the un-depressed position in the illustrated embodiment. The height of the cover region above the base is indicated as "h", and the diameter of the cover region in the un-depressed position is indicated as "d". It can be appreciated that the cover region 120 can have any desired shape in the un-depressed position such as a cuboidal cover region with rounded edges or similar shapes. In some embodiments, the cover 106 can include a diving board configuration. In some embodiments, the cover region 120 can comprise a cover region geometry that includes cover region edges 122 and 124. The cover region edges 122 and 124 define a cover region wall thickness "a". The cover region 120 can move a specific distance when a predetermined depression force is applied on the cover region 120. The predetermined depression force can cause the cover region 120 to move in a controlled manner from the un-depressed position, to a depressed position, shown in FIGS. 2 and 3. When the cover region is in the depressed position, the cover region 120 provides access to the lancet 104.

Figure 4A:
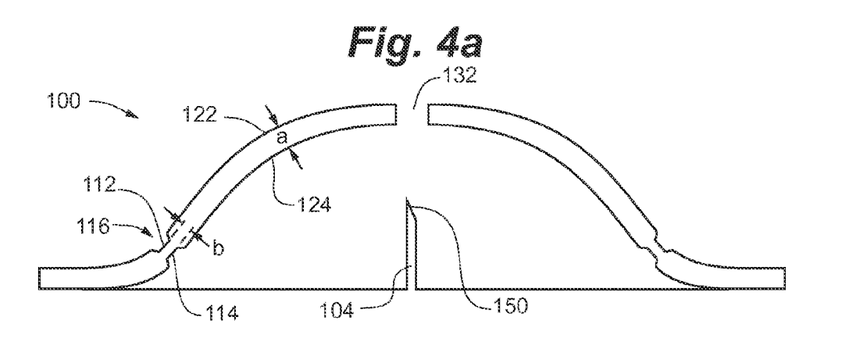
FIG. 4(a) is a front elevation view of a lancet device according to embodiments of the invention with the cover in the un-depressed position.
Figure 4B:
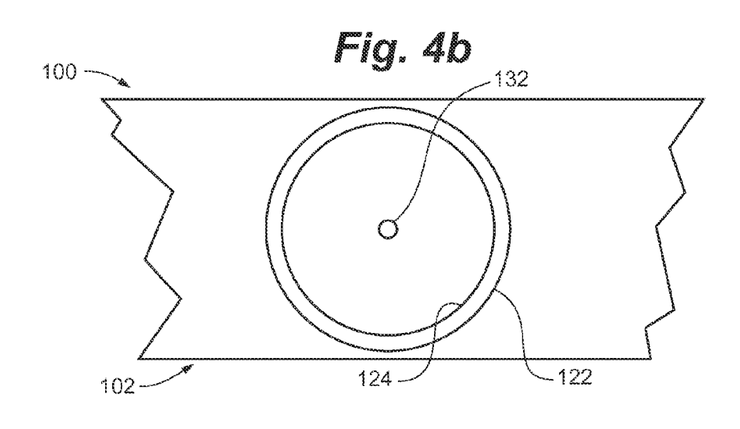
FIG. 4(b) is a top plan view of a lancet device of FIG. 4(a).

In some embodiments, the cover 106 can include a peripheral hinge 116 near the peripheral edge 110 as shown in FIG. 4(a). In some embodiments, the peripheral hinge 116 can include peripheral hinge geometry. The peripheral hinge geometry can comprise a variety of configurations. For example, in some embodiments, peripheral hinge edges 112, 114 can define a peripheral hinge wall thickness "b" as shown in FIG. 4(a). In some embodiments, the peripheral hinge geometry can include peripheral hinge edge 112 or peripheral hinge edge 114 but not both. In some embodiments, the peripheral hinge geometry can include rounded or angular hinges. Peripheral hinge edges 112, 114 can include or can be replaced by curved, angled or box-shaped notches or projections near the peripheral edge 110. For instance, the notches can be angled as V or H-shaped notches with a projection of complementary shape. The notches or projections can act as a hinge joint and can resemble a knee or an elbow joint. It can be appreciated that other hinge shapes that introduce a similar effect can be included without any loss of functionality. The peripheral hinge 116 facilitates the controlled movement of the cover 106 from the un-depressed position to the depressed position upon application of a predetermined depression force.

In many embodiments, the peripheral hinge geometry can differ from the cover region geometry. For example, the cover region thickness "a" can be different from the peripheral hinge thickness "b". In some embodiments, the peripheral hinge wall thickness "b" is between approximately 25% and approximately 50% of the cover region wall thickness "a". In some embodiments, the peripheral hinge wall thickness "b" is less than half of the cover region wall thickness "a". In some embodiments, the peripheral hinge wall thickness "b" is between ⅔ and ¾ the cover region wall thickness "a". In some embodiments, the peripheral hinge wall thickness "b" is less than ⅔ the cover region wall thickness "a". In some embodiments, the peripheral hinge wall thickness "b" is less than ¾ the cover region wall thickness "a". The cover region thickness "a" and the peripheral wall hinge thickness "b" can be varied during fabrication of the device.

The lancet device 100 can be configured such that the cover 106 moves from the un-depressed position to the depressed position upon application of a predetermined force that a typical user would be capable of applying. In some embodiments, the predetermined depression force can be between approximately 500 and approximately 1500 grams. In some embodiments the predetermined depression force can be between approximately 700 grams and approximately 2000 grams. In some embodiments, the predetermined depression force can be between approximately 800 grams and approximately 1200 grams. In some embodiments, the predetermined depression force can be between approximately 700 grams and approximately 800 grams. In some embodiments, the predetermined depression force can be between approximately 800 grams and approximately 900 grams. In some embodiments, the predetermined depression force can be between approximately 900 grams and approximately 1000 grams. In some embodiments, the predetermined depression force can be between approximately 1000 grams and approximately 1100 grams. In some embodiments, the predetermined depression force can be between approximately 1100 grams and approximately 1200 grams. In some embodiments, the predetermined depression force can be between approximately 1200 grams and approximately 1300 grams. In some embodiments, the predetermined depression force can be between approximately 1300 grams and approximately 1400 grams. In some embodiments, the predetermined depression force can be between approximately 1400 grams and approximately 1500 grams. In some embodiments, the predetermined depression force can be between approximately 1500 grams and approximately 1600 grams. In some embodiments, the predetermined depression force can be between approximately 1600 grams and approximately 1700 grams. In some embodiments, the predetermined depression force can be between approximately 1700 grams and approximately 1800 grams. In some embodiments, the predetermined depression force can be between approximately 1800 grams and approximately 1900 grams. In some embodiments, the predetermined depression force can be between approximately 1900 grams and approximately 2000 grams. In some embodiments, the predetermined depression force can be greater than 2000 grams. The distance traveled by the cover region 120 between the un-depressed (shown as dashed lines in FIGS. 2-3) and the depressed position, is indicated by a depression depth "f" in FIGS. 2-3. The depression depth "f" can be between approximately 0.2 millimeters and approximately 4 millimeters when the predetermined force is applied. Different configurations with different required depression forces may be offered for different kinds of users. The depression depth can be adjusted by including a design of the cover region 120 with a diameter "e" and a height "g" that are different from the illustrated diameter "d" and the illustrated height "h".

Figure 2:
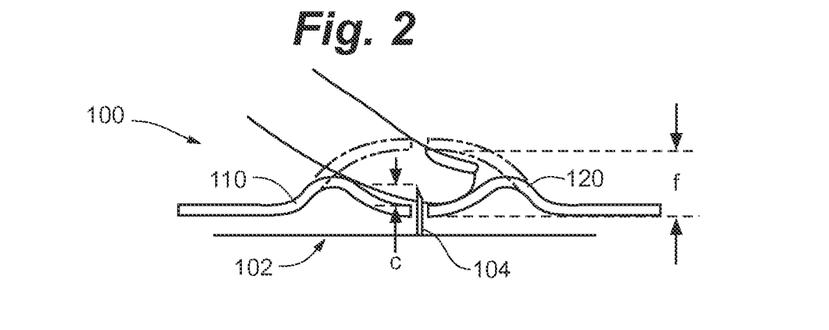
FIG. 2 is a front elevation view of the lancet device of FIG. 1 with the cover in a depressed position.
Figure 3:
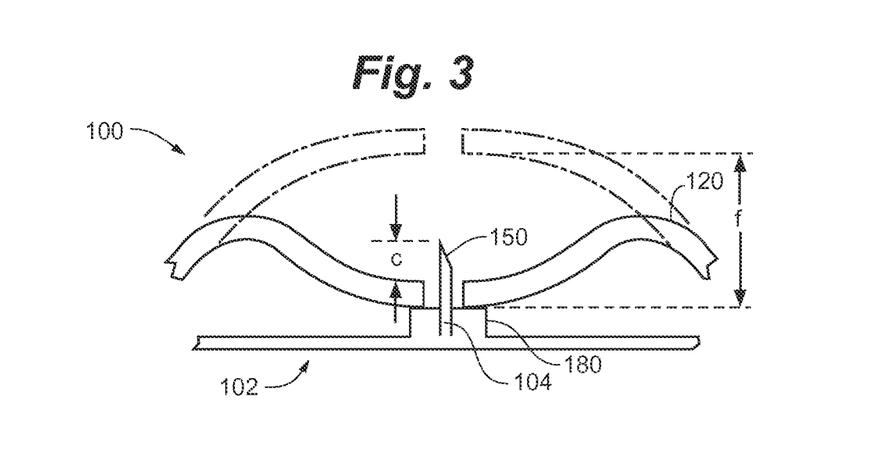
FIG. 3 is a front elevation view of a lancet device according to embodiments of the invention with the cover in the depressed position.
Figure 5A:
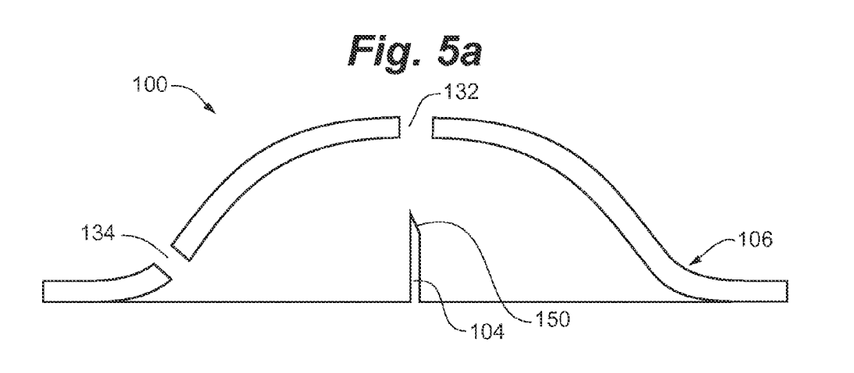
FIG. 5(a) is a front elevation view of a lancet device according to embodiments of the invention with the cover in the un-depressed position.
Figure 5B:
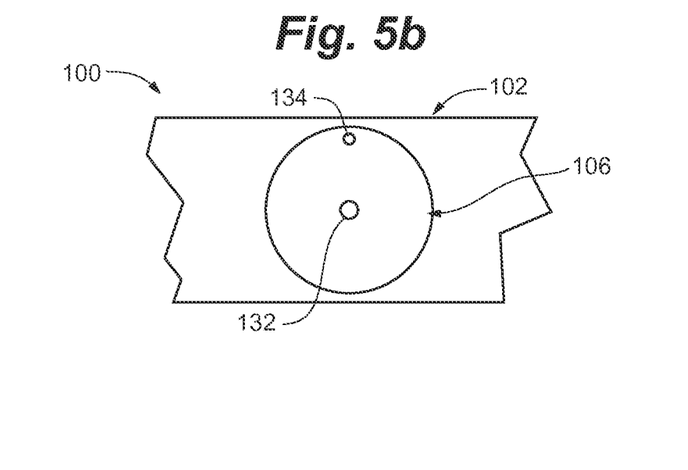
FIG. 5(b) is a top plan view of the lancet device of FIG. 5(a).

In some embodiments, the cover 106 can include a lancet aperture 132 through which the lancet 104 is configured to protrude when the cover 106 is in a depressed position. The lancet aperture 132 is illustrated as a circular opening in FIG. 5(b), but can also be of other shapes. The diameter or the opening size of the lancet aperture 132 is at least equal to the thickness of the lancet as shown in FIG. 5(a) so that the lancet 104 protrudes out of the lancet aperture 132 when the cover 106 is in the depressed position. The lancet aperture 132 may be introduced in the cover region 120 by cutting or tearing the cover region 120 appropriately to the required geometry and dimensions of the lancet aperture 132. The lancet 104 can protrude through the lancet aperture 132 to a protrusion height "c" when the cover 106 is in the depressed position as shown in FIGS. 2-3. In some embodiments, the protrusion height "c" of the lancet 104 can be between approximately 0.3 millimeters and approximately 1.2 millimeters. The protrusion height "c" can be selected so that optimal quantity of biological sample is collected. For example, if the lancet device is used for collecting blood from a user by lancing the user's finger skin, an appropriate protrusion height "c" can ensure optimal quantity of blood is drawn from the user's finger and at the same time minimizing pain in the user due to lancing. Anatomical features such as thickness of the finger skin, pain tolerance, and blood flow through a user's blood vessels can be considered by a user in deciding on a suitable protrusion height of the lancet. A user can, for instance, apply less force on the cover region 120 of the lancet device 100, causing the protrusion height "c" to be lower, than in the case if the user where to apply more force on the cover region 120.

In some embodiments, the cover 106 can be configured to provide an auditory and/or tactile response as the cover 106 moves from the un-depressed position to the depressed position upon application of the predetermined depression force. When the lancet device 100 is used to collect a biological sample such as a blood sample from a user by lancing the user's skin, the auditory and/or tactile response can facilitate lower pain perception by a user. In some embodiments, the cover 106 is engineered from a material such that the material provides an auditory response when it moves from the un-depressed position to the depressed position. In some such embodiments, the auditory response can be a pleasing sound (e.g., a snapping sound) when the force due to the user's finger pressure on the cover 106 equals the predetermined depression force. The pleasing sound can cause the user to perceive lower pain due to lancing. In some such embodiments, the pleasing sound can be accompanied by a tactile response (e.g., a sensation that the cover 106 has snapped past a threshold point), which can cause lower pain perception. In some embodiments, the tactile response can be provided with little or no auditory response. In some embodiments, the lancet 104 does not vibrate during lancing leading to lower pain perception.

Figure 6:
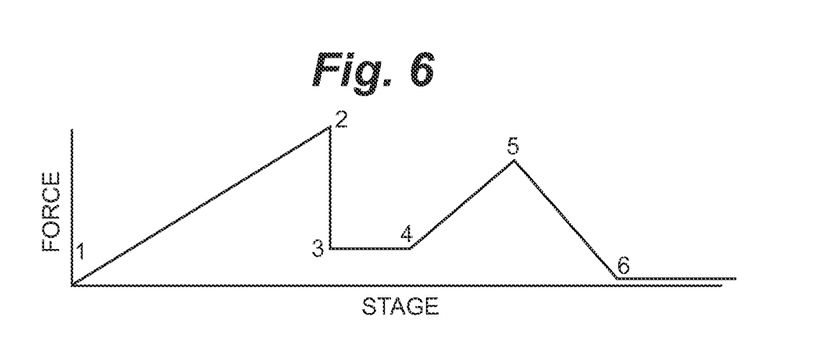
FIG. 6 is a graph that shows the force applied to the lancet cover at various stages of use of a lancet device.

In some embodiments, the cover 106 can be configured to provide a force response. This force response is illustrated in FIG. 6. The force response facilitates movement of the cover 106 from the depressed position back to the un-depressed position upon removal of the predetermined depression force. In some embodiments, the cover 106 is made of materials that can be engineered to provide the force response. The force response can be used to facilitate lower pain perception by a user. As shown in FIG. 6, the cover 106 can be configured such that when the force due to finger pressure equals the predetermined depression force (FIG. 6, Point 2), the design features of the cover 106 can move from resisting the depression force to acceleration in downward movement until it reaches a designed stop (FIG. 6, Point 3). After the skin has been lanced due to this movement, the depression force can lift from the cover (FIG. 6, Point 4). The design features of the cover region 120 can create a spring-like response accelerating the cover 106 back up which pushes upward and lifting the skin off the lancet 104 (FIG. 6, Point 5). Finally the skin is lifted from the cover 106 so that no force is applied (FIG. 6, Point 6).

In some embodiments, the cover 106 can include a release aperture 134 to release trapped air that might impede controlled movement of the cover 106. The release aperture 134 can be located near the peripheral edge 110 of the cover 106. The release aperture 134 is illustrated as a circular opening in FIG. 5(b). It can be appreciated that the release aperture 134 can be of other geometrical shapes without loss of functionality. The release aperture 134 can be of a size on the order of the size of the lancet aperture 132. Any trapped air near the peripheral edge 110 of the cover 106 can resist movement of the cover region 120 toward the depressed position when the predetermined force is applied. The release aperture 134 allows the trapped air near the peripheral edge 110 (the air cannot escape through the lancet aperture 132 because the lancet aperture 132 is essentially sealed by the user's skin) to escape through the release aperture 134 outwardly from the peripheral edge 110, thereby facilitating controlled movement of the cover region 120 between the un-depressed and depressed positions.

Figure 7:
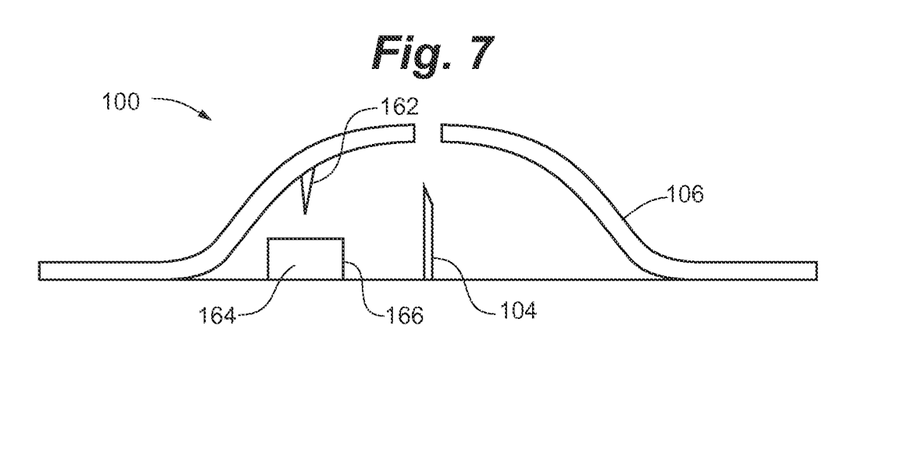
FIG. 7 is a front elevation view of a lancet device according to embodiments of the invention with the cover in the un-depressed position.

In some embodiments, the cover 106 can include a spike 162 extending toward the base 102. The spike can be of a material similar to the lancet 104, or other suitable material. In this embodiment, the lancet device 100 can include a cavity 164 on the base 102 under the cover 106. The cavity 164 may include a cavity wall 166 that holds pressurized gas. As the cover 106 moves from the un-depressed position to the depressed position, the spike 162 can moves toward the cavity 164, eventually piercing the cavity wall 166. The cavity 164 can release pressurized gas upon being pierced by the spike 162. The released gas can exert pressure on the cover 106 to push the cover 106 from the depressed position back to the un-depressed position. The pressurized gas combination can be used in addition to the cover 106 with engineered materials capable of providing a force response.

Figure 8:
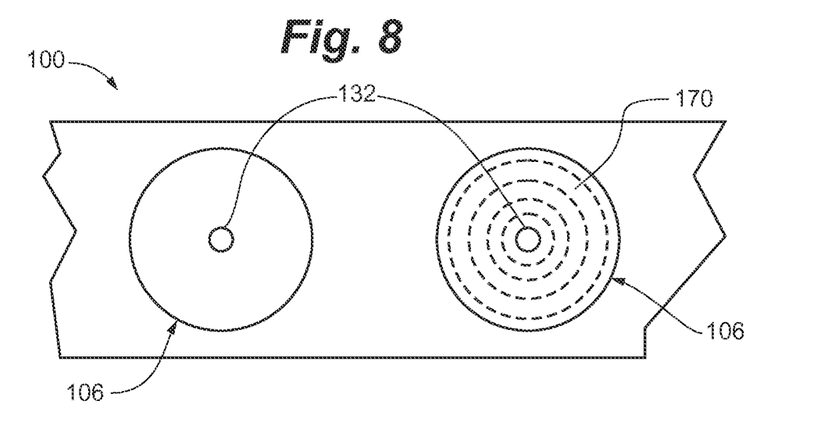
FIG. 8 is a top plan view of a lancet device according to embodiments of the invention.

In some embodiments, the base 102 can include a visual indicator 170 that shows if the cover has been moved from the un-depressed position to the depressed position as shown in FIG. 8. The base 102 can be made of a material that can be configured to provide a pattern or a color change. The color or pattern change can occur when the applied force on the cover region 120, such as due to finger pressure when lancing, exceeds the predetermined depression force. The visual indicator 170 can include a color or pattern changing surface made of materials such as pressure sensitive coating or films operably coupled to the base 102. The visual indicator 170 facilitates a user in identifying whether a lancet device was previously used and allow for single use of a lancet device. Visual indicators other than those shown may be incorporated into lancet devices in various embodiments of the present invention.

In some embodiments, the base 102 can include a stop 180 under the cover 106. The stop 180 can be configured to dictate a distance by which the lancet 104 is configured to protrude through the lancet aperture when the cover 106 is in the depressed position. The size of the stop 180 can be determined during manufacture based on the depth of insertion of the lancet 104. The stop 180 is illustrated as a rectangular projection in FIG. 3. It can be appreciated that the stop 180 can have any desired shape, such as a hemispherical projection or other shapes. The stop 180 can be fabricated from materials similar to the base 102. The stop 180 can be included with the base 102 as a single component during fabrication.

Figure 9A:
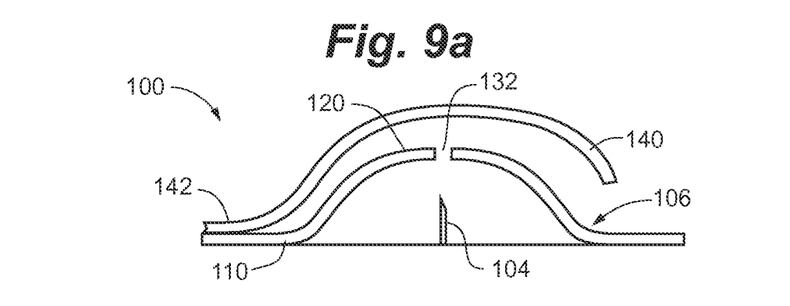
FIG. 9(a) is a front elevation view of a lancet device according to embodiments of the invention with the cover in the un-depressed position, and a cap in a capped position.
Figure 9B:
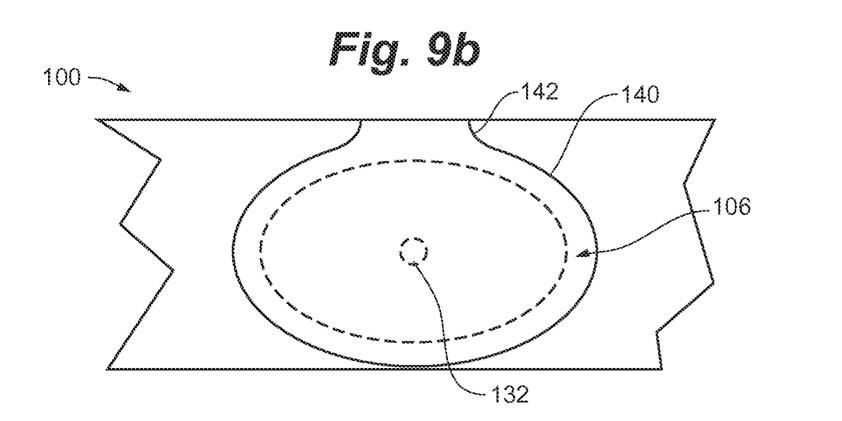
FIG. 9(b) is a top plan view of the lancet device of FIG. 9(a) with the cap in the capped position.

In some embodiments, the lancet device can include a cap 140 as shown in FIGS. 9(a)-9(b). The cap 140 can operably couple with the base 102 by a hinge connection 142 as shown in the illustrated embodiment, or by similar mechanical fasteners. The cap 140 can be made of materials similar to that of the base 102. The cap 140 can be positioned from a capped position to an uncapped position. In the capped position, the cap 140 is in close proximity to the base 102, and encloses the cover 106, thereby preventing access to the lancet 104. In the uncapped position, the cap 140 facilitates access to the lancet 104. The cap 140 can be configured to act as a sterile barrier when in the capped position to isolate the lancet 104 from contaminants.

In use, a lancet device 100 such as those discussed elsewhere herein can be used for collecting blood from a user for monitoring glucose. In some embodiments, the lancet device 100 can be used for collecting similar biological samples. A user can apply a force on the cover region 120. The force applied by the user can be due to finger pressure. The force applied on the cover region 120 may increase as indicated by the force ramp during stages 1-2 in FIG. 6. If the force applied by the user is equal to or greater than a predetermined force, the cover 106 can move from an un-depressed position in which the cover region covers the lancet to a depressed position during stage 2-3 in FIG. 6. The lancet 104 protrudes through the lancet aperture 132 in the depressed position and exposes biological fluid. A quantity of the biological fluid as the biological sample can be collected during stages 3-4 in FIG. 6.

When the user stops applying force on the cover region 120, the cover region 120 exerts a pushing force opposite to the force applied by the user. The pushing force can be as a result of tension in the cover region 120 due to its material elasticity and/or by one or more mechanical tensioning elements included in the cover region as discussed elsewhere herein. The pushing force from the cover region 120 gradually increases as shown by the force ramp during stages 4-5 in FIG. 6. When stage 5 is reached, the cover region 120 has moved from the depressed position back to the un-depressed position. The user can then remove the finger from the lancet device and proceed to provide the biological sample for the desired purpose.

Some embodiments of the present invention involve a biological test kit 200. The biological test kit 200 can include a reusable module 210 and a disposable module 220. In some embodiments, the disposable module 220 and reusable module 210 can be fabricated as a single, integral module and cannot be modularly connected to and disconnected from one another. In many embodiments, the disposable module 220 can be removably connected with the reusable module 210. The biological test kit 200 is illustrated as having a rectangular shape in FIGS. 10a and 10b, but can have any desired shape such as square or oval without loss of functionality. In the illustrated embodiment, the biological test kit has a length "x", a width "y" and a thickness "z". The thickness "z" of the biological test kit 200 can be substantially less than the length "x" or the width "y". The biological test kit 200 can be fabricated by molding a rigid polymer material such as plastic or by machining a similar material. In some embodiments, the thickness "z" can be less than or equal to ½ inch. In some embodiments, the thickness "z" can be less than or equal to 0.35 inches. In some embodiments, the thickness "z" can be less than or equal to 0.2 inches.

Figure 10A:
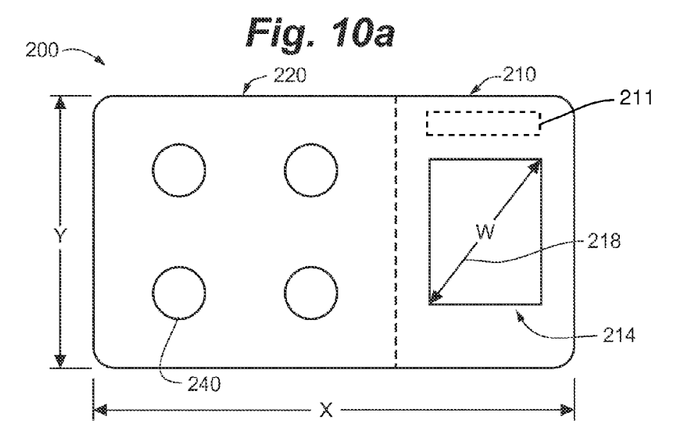
FIG. 10(a) is a top plan view of a biological test kit according to embodiments of the invention.
Figure 10B:
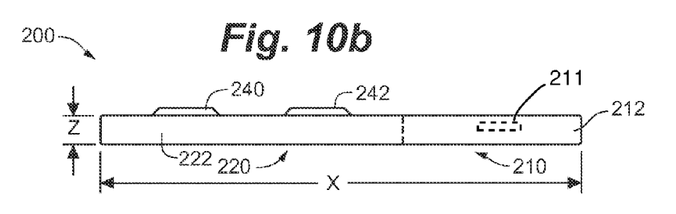
FIG. 10(b) is a front elevation view of the biological test kit of FIG. 10(a).

In some embodiments, the reusable module 210 can include a reusable module housing 212, measuring equipment 214, and a reusable module connector 216. The reusable module housing 212 can include a generally planar support surface to support the measuring equipment 214. In some embodiments, the reusable module housing 212 may include a second support surface. The second support surface can house the reusable module connector 216. The planar support surface and the second support surface can be any of the surfaces of the reusable module 210. In the illustrated embodiment, the planar support surface supporting the measuring equipment 214 is the top surface of the reusable module housing 212. The support surface that houses the reusable module connector 216 is a lateral surface of the reusable module housing 212. Any of the top, bottom, front, back or lateral surfaces can house the measuring equipment 214 and reusable module connector 216 without loss of functionality of the biological test kit 200.

The measuring equipment 214 and the reusable module 210 connector can be supported by the reusable module housing 212. The measuring equipment 214 can be configured to measure a property of a biological sample. The measuring equipment 214 can include a sensor that can measure a specific property of the biological sample by electro-chemical means or other methods known in the arts. The measuring equipment 214 can, for instance, be configured to measure blood glucose level. For example, a chemical reaction can occur between a specific quantity of blood glucose, and an enzyme or a reagent that generates an electric current at an electrode. The measuring equipment 214 can then be configured to sense the electric current and calibrated to correlate a specific value of an electric current to a blood glucose level.

In some embodiments, the reusable module 210 can include a display monitor 218 supported by the reusable module housing 212 and configured to display the measured property. The display monitor 218 can be a LCD panel or LED or similar display device that can display the measured property and/or other relevant information. The display monitor 218 can be supported by the reusable module housing 212 by any of the known methods, including microfabrication techniques. In the illustrated embodiment, the display monitor 218 is a rectangular panel of diagonal length "w." It may be appreciated that the display monitor 218 can be of any desired size or shape to display the measured property (e.g., as alphanumeric characters). The display monitor 218, for instance, can display blood glucose level as a numerical value in milligrams per deciliter, when the biological test kit 200 collects blood from users for diabetes management.

The disposable module 220 can include a disposable module housing 222, at least one lancet station, at least one strip station, and a disposable module connector 226. The disposable module housing 222 can be made of a rigid polymer material such as plastic. The disposable module housing 222 may include a support surface to house at least one lancet station and one strip station, and can be adapted to provide support to multiple lancet and strip stations or other components. In some embodiments, the disposable module housing 222 can include a second support surface that house the disposable module connector 226.

The first lancet station 240 can be supported by and is stationary relative to the disposable module housing 222. The first lancet station 240 is illustrated in the embodiment as comprising a circular station, though other configurations are contemplated as within the scope of this disclosure. The first lancet station 240 can include a device such as the lancet device 100 described elsewhere herein. The first lancet station 240 can comprise a cover supported by the disposable module housing 222. The cover can be fabricated from a polymeric material with sufficient elasticity to depress to a specific height upon application of a predetermined force. The cover can include an aperture that provides access to a lancet. The lancet can be supported by the disposable module housing. The first lancet station 240 can include any of the embodiments of the lancet device 100. The first lancet station 240 can facilitate the generation of a first biological sample. The first biological sample, for instance, can be a small quantity of blood for monitoring blood glucose.

The first strip station 250 can be supported by the disposable module housing 222. The first strip station 250 can include a first biological strip 260 configured to receive the first biological sample. The first biological strip 260 can be rectangular with a thickness much smaller than length and width. The first biological strip 260 can be fabricated from a sheet of polymeric material with coatings to generate a signal that can be input to the measuring equipment 214 when exposed to the first biological sample. The first biological strip 260 can include a coating of an enzyme or a reagent that can electro-chemically react with the first biological sample. The first strip station 250 can be configured to provide the first biological sample to the measuring equipment 214 for measurement of the property.

The disposable module connector 226 can be supported by the disposable module housing 222 and can be modularly connectible to the reusable module connector 216. In some embodiments, the disposable module connector 226 and the reusable module connector 216 can together comprise an interlocking fastener. The disposable and reusable module connectors 226 and 216 can be mechanical connectors such as clips, latches, hooks and loops or similar fasteners. The disposable and reusable module connectors 226 and 216 can be adhesive connectors.

Figure 12:
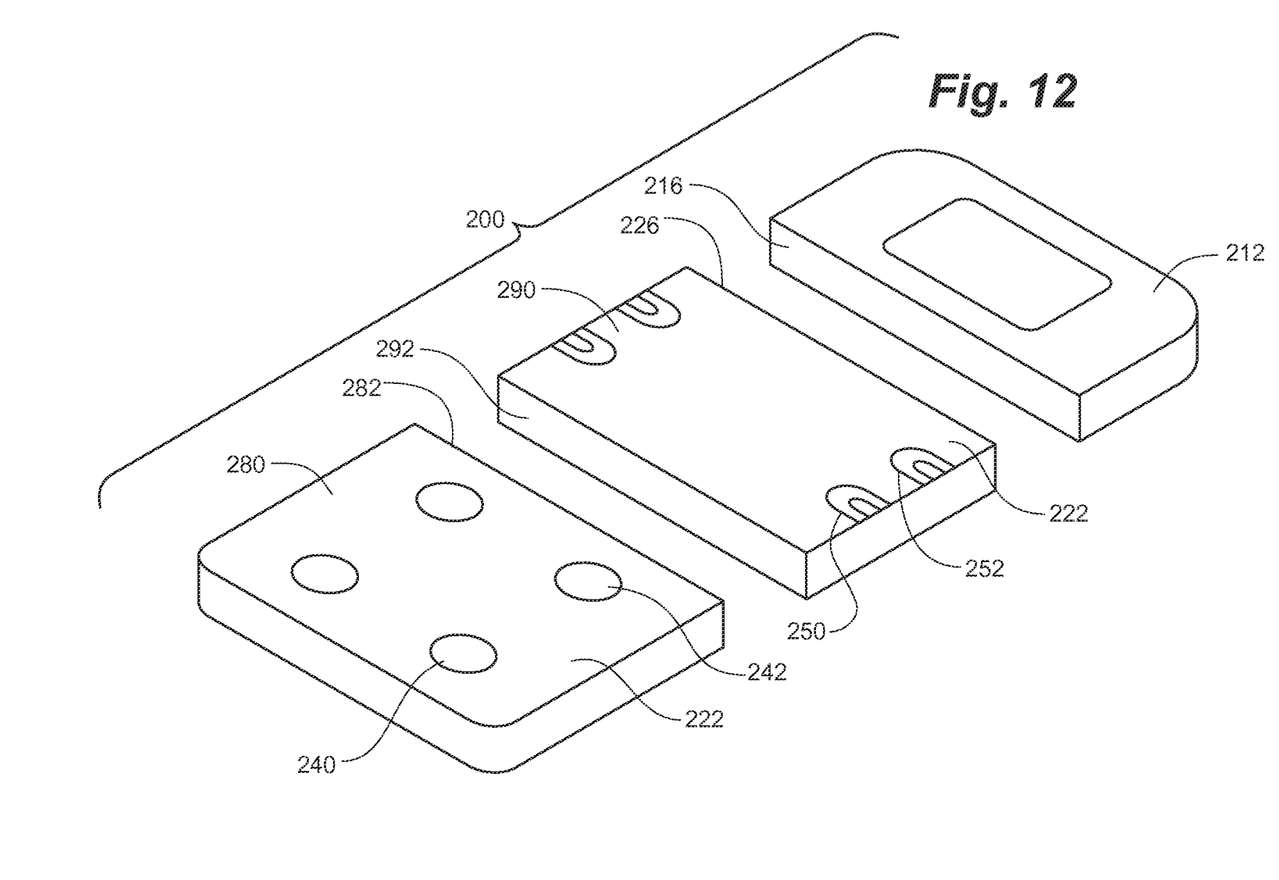
FIG. 12 is an exploded perspective view of a biological test kit according to embodiments of the invention.

In some embodiments, the disposable module housing 222 can include first and second sub-module housing 280, 290 as shown in FIG. 12. The first and second sub-module housing 280, 290 can be fabricated from similar materials as the disposable module 220. The first sub-module housing 280 can be configured to support the first lancet station 240. The first sub-module housing 280 can include a first sub-module connector 282. In the illustrated embodiment, the first sub-module housing 280 supports the first lancet station 240 on a generally planar top surface of the first sub-module housing 280. The first sub-module connector 282 is supported on a generally planar lateral surface of the first sub-module housing 280. Any of the top, bottom, front, back or lateral surfaces of the first sub-module housing 280 can support the first sub-module connector 282.

The second sub-module housing 290 can be configured to support the first strip station 250. The second sub-module housing 290 supports the first strip station 250 on a generally planar top surface. The second sub-module housing 290 can include a second sub-module connector 292 that is modularly connectible to the first sub-module connector 282. The second sub-module connector 292 is shown supported on a generally planar lateral surface of the second sub-module housing 290. Any of the top, bottom, front, back or lateral surfaces of the second sub-module housing 290 can support the second sub-module connector 292. The first and second sub-module connectors 282 and 292 can removably connect by mechanical means such as clips, latches, hook and loop fasteners. An adhesive film can be applied on the first and second sub-module connectors 282 and 292. It can be appreciated that either of the first sub-module 280 or second sub-module 290 can be fabricated together with the reusable module 210 to form a non-separable module. In such an embodiment, the non-separable module can be removably connected with the remaining sub-module by connectors similar to those discussed elsewhere herein. Many variations are contemplated depending on the desired application.

In some embodiments, the biological test kit 200 can have an overall thickness "z" of approximately 12.7 millimeters. In some embodiments, the biological test kit 200 can have a thickness "z" of less than one centimeter and approximately 5 millimeters. In some embodiments, the biological test kit 200 can have a length of less than 10 centimeters and approximately 8 centimeters. In some embodiments, the biological test kit 200 can have a width of approximately 5 centimeters. The biological test kit 200 can be fabricated from polymers such as sheets of plastic by machining the sheets to specific dimensions and providing the reusable and disposable module housings 212, 222 with means to couple to a first lancet station 240, a first strip station 250, measurement equipment 214, display monitor 218 and other components as discussed above. The biological test kit 200 can be fabricated by techniques such as molding.

In some embodiments, the disposable module can include a second lancet station 242 and a second strip station 252. The second lancet station 242 and the second strip station 252 can be similar in size and shape to the first lancet station 240 and the first strip station 250. The second lancet station 242 and the second strip station 252 can be supported by the disposable module housing 222. The second lancet station 242 can be configured to remain stationary relative to the disposable module housing 222. The second lancet station 242 can be configured to facilitate generation of a second biological sample. The second biological sample can be similar to the first biological sample. The second biological sample can be substantially distinguishable from the first biological sample in composition.

The second strip station 252 can include a second biological strip 262 configured to receive the second biological sample. The second biological strip 262 can be of a size and shape to be supported by the second strip station 252. The second biological strip 262 can be fabricated from a sheet of polymeric material with coatings to generate a signal that can be input to the measuring equipment 214 when exposed to the second biological sample. The second biological strip 262 can include a coating of an enzyme or a reagent that can electro-chemically react with the second biological sample. The second strip station 252 can be configured to provide the second biological sample to the measuring equipment 214 for measurement of the property.

Figure 11:
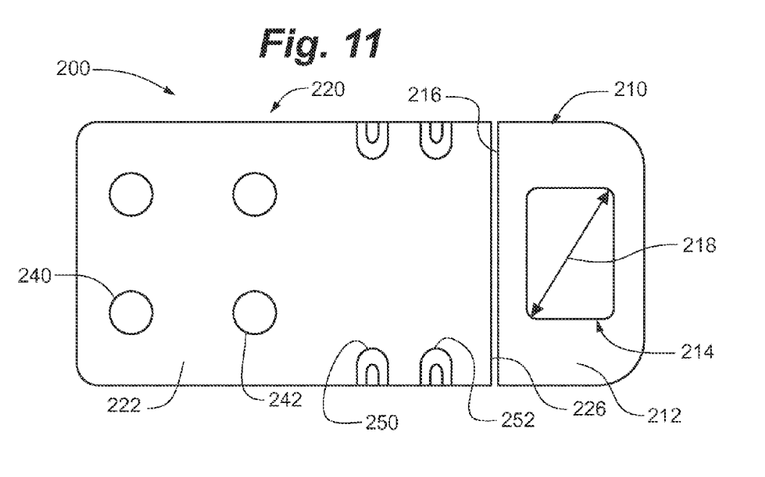
FIG. 11 is an exploded front elevation view of a biological test kit according to embodiments of the invention.

It should be understood that, while embodiments discussed elsewhere herein include one or two lancet stations and one or two strip stations, some biological test kits can have other numbers of lancet stations and/or strip stations. For example, some embodiments include four lancet stations (e.g., the biological test kit 200 of FIG. 11). Some embodiments include different numbers of lancet stations, such as three, five, six, and so on. Some embodiments include different numbers of strip stations, such as three, five, six, and so on. In many embodiments, the number of lancet stations is equal to the number of strip stations. Such embodiments can facilitate one use of a lancet station for each strip station. In some embodiments, the number of lancet stations and/or strip stations on a disposable module can be tied to the number of times per day a category of patients must measure a biological sample. For example, if a significant percentage of diabetic patients are encouraged to check their blood glucose levels five times per day, a biological test kit can be offered that includes five lancet stations and five strip stations so that the patients can use one disposable module per day.

In some embodiments, the measuring equipment 214 of the biological test kit 200 can include a correlation mechanism configured to identify a measured biological sample as having originated from the first strip station 250 or the second strip station 252 (or other strip stations). The measuring equipment 214 can be configured to provide whether the measured biological sample originated from the first strip station 250 or the second strip station 252 to the display monitor 218 for display in a manner known in the art, such as integrated circuit board connections, or similar means. In the embodiment shown in FIGS. 10a and 10b, the biological test kit 200 includes four lancet stations and four strip stations. It can be appreciated that more than two lancet and strip stations can be included in the biological test kit 200. The measuring equipment 214 can be adapted to include a correlation mechanism that can identify a measured biological sample as having originated from one of the many strip stations.

In some embodiments illustrated in FIGS. 10a and 10b, the reusable module 210 can include a wireless transmitter 211 supported by the reusable module housing 212. The wireless transmitter 211 can be configured to transmit a signal representative of the measured property to a separate device for display. The wireless transmitter 211 can be a BLUETOOTH transmitter that can interface with a mobile device that is adapted with a BLUETOOTH receiver, or any similar transmission device. The mobile device may be a cell phone or tablet devices that can receive signals transmitted wirelessly, and store the measured property.

Figure 13:
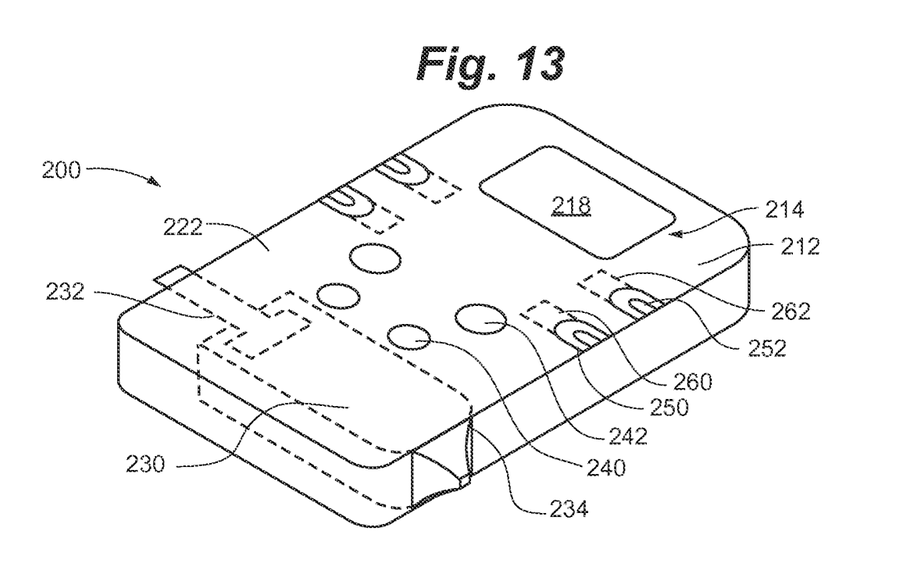
FIG. 13 is a perspective view of a biological test kit according to embodiments of the invention.

In some embodiments, the disposable module 220 can include an insulin delivery device connector 234 supported by the disposable module housing 222 as shown in FIG. 13. The insulin delivery device connector 234 can be configured to detachably connect the disposable module 220 to an insulin delivery device 230. The insulin delivery device connector 234 can be supported by any of the top, bottom, front, back or lateral surfaces of the disposable module housing. The insulin delivery device connector 234 can be a clip, latch, hook-and-loop fastener or similar mechanism that can removably connect with an insulin delivery device 230. The insulin delivery device connector 234 can be an adhesive coating or film. The insulin delivery device 230 can be an insulin storage container with a syringe 232 for delivering insulin in users who monitor and manage blood glucose levels. The insulin delivery device 230 can be removably connected to the reusable module 210 by the insulin delivery device connector 234. It should be understood that the disposable module 220 and reusable module 210 need not be removably connected and be fabricated as a single module. In such an embodiment, the insulin delivery device 230 can be removably connected with the single module by the insulin delivery device connector 234. It should also be understood that the insulin delivery device 230 can be supported by the reusable module 210 in some embodiments.

Figure 14:
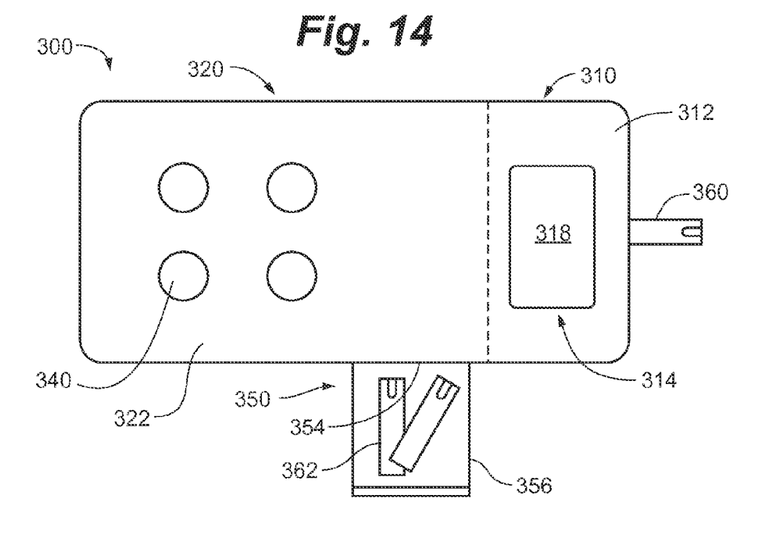
FIG. 14 is a top plan view of a biological test kit according to embodiments of the invention.

FIG. 14 shows a biological test kit 300 according to some embodiments. The biological test kit 300 can include a reusable module 310 and a disposable module 320. In some embodiments, the disposable module 320 and reusable module 310 can be fabricated as a single module. In many embodiments, the disposable module 320 and the reusable module 310 can be fabricated as separate modules removably connectable to one another. The reusable module 310 can include a reusable module housing 312, measuring equipment 314 and a reusable module connector (not shown). The disposable module 320 can include a disposable module housing 322, a first lancet station 340, a first strip station 350, and a disposable module connector (not shown). The disposable module 320 can be removably connected to the reusable module 310 by the disposable module connector and the reusable module connector. The first strip station 350 can include a slot 354 in the disposable module housing and a strip container 356 positioned in the slot 354. The slot 354 and the strip container 356 can be fabricated from materials such as plastic. The size of the slot and the strip container 356 are such that the strip container 356 can store a first biological strip 360 (or other biological strips) and the strip container 356 can slide in and out of the slot 354. The strip container 356 can be configured to slide into and out of the slot 354 between a closed position and an open position. The strip container 356 can be adapted to provide access to the first biological strip 360 when in the open position, as shown in FIG. 13. The strip container 356 can be configured to house a second biological strip 362 (or other biological strips). It can be appreciated the slot 354 and the strip container 356 can be positioned on the reusable module 310. In some embodiments of the biological test kit 300, the reusable and disposable modules may not form a removable connection and are fabricated as a non-separable or integral module. In such an embodiment, the slot 354 and the strip container 356 can be positioned on the non-separable module and configured similar to means discussed above.

Figure 15:
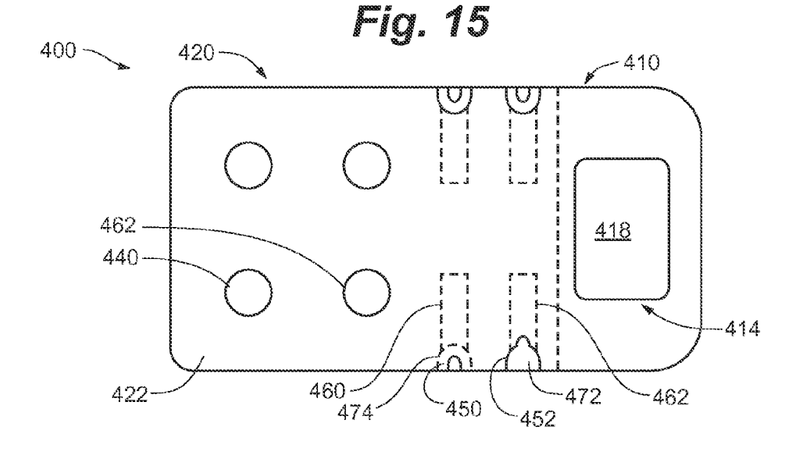
FIG. 15 is a top plan view of a biological test kit according to embodiments of the invention.
Figure 16:
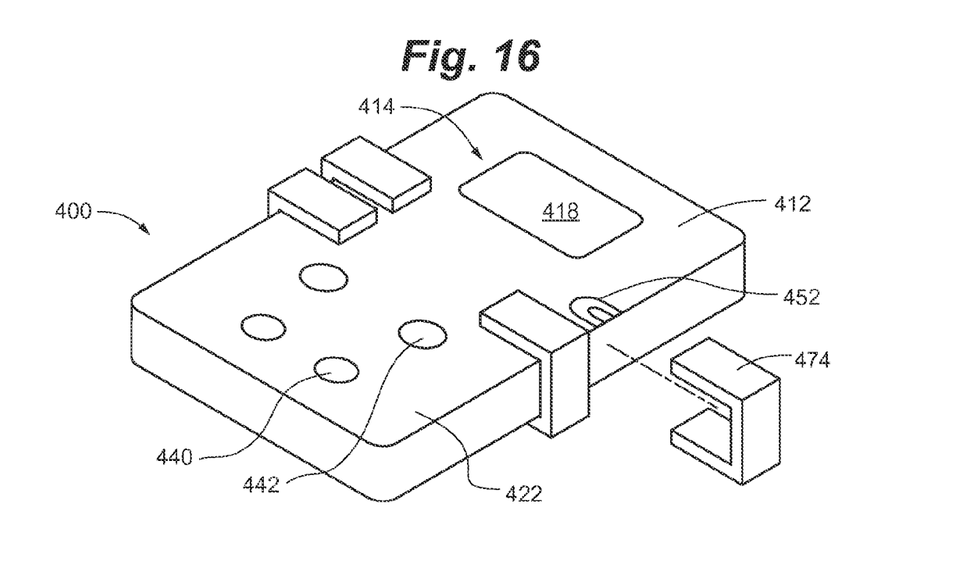
FIG. 16 is a perspective view of a biological test kit according to embodiments of the invention.
Figure 17:
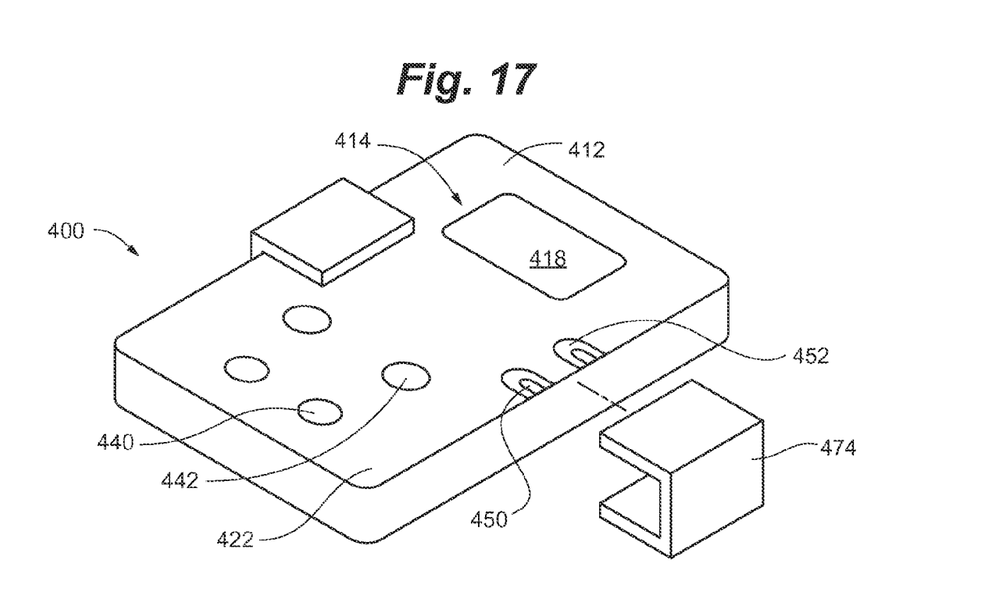
FIG. 17 is a perspective view of a biological test kit according to embodiments of the invention.

FIGS. 15-17 illustrate a biological test kit 400 according to some embodiments. The biological test kit 400 can include a reusable module 410 and a disposable module 420. The disposable module 420 and reusable module 410 can be fabricated as a single module. The reusable module 410 can include a reusable module housing 412, measuring equipment 414 and a reusable module connector 416. The disposable module 420 can include a disposable module housing 422, a first lancet station 440, a first strip station 452, and a disposable module connector (not shown). The disposable module 420 can be removably connected to the reusable module 410 by the disposable module connector 426 and the reusable module connector 416. The first strip station 452 can include a recess 472 defined in the disposable module housing 422 and a strip station cover 474. The recess 472 shown as a shaded portion in FIG. 14 can be configured to hold a first biological strip 462. The recess 472 can be cut or machined on the disposable module housing 422 to accommodate the first biological strip 462. A second strip station 450 can include a second biological strip 460 positioned in a recess similar to the recess 472 and covered by the strip station cover 474. The strip station cover 474 and the second biological strip 460 are indicated by dashed lines in FIG. 14. It should be understood that such an embodiment can include any number of strip stations, as discussed elsewhere herein.

The strip station cover 474 can be removably connected to the disposable module housing 422. The strip station cover can be configured to cover the recess 472 and prevent access to the first biological strip 462 when in a covered position. The strip station cover 474 can be configured to permit access to the first biological strip 462 when in an uncovered position. The strip station cover 474 can be removably connected to the disposable module housing 422 by mechanical fasteners or adhesives. The strip station cover 474 can be a film containing an adhesive to removably connect to the disposable module housing 422. The strip station cover 474 can be peeled to remove the adhesive connection between the strip station cover 474 and the disposable module housing 422. In the illustrated embodiment shown in FIG. 15, strip station cover 474 prevents access to the first biological strip 462 in a covered position. A second biological strip 460 can be accessed when a corresponding strip station cover is in an uncovered position. FIGS. 16 and 17 show the strip station cover 474 according to some embodiments. In the illustrated embodiments, the strip station cover 474 includes a groove that is configured to engage with the disposable module housing 422 by a friction fit. In the illustrated embodiments in FIGS. 15-17, the first and second strip stations 450 and 452 are located on the disposable module 420. It can be appreciated that the biological test kit 400 can be fabricated as a single component without two modules that can be removably connected (E.g.: the disposable and the reusable module forming a single module). In such an embodiment, the strip station cover 474 forms a friction fit with the single module.

In use, a biological test kit such as those discussed elsewhere herein can be used for managing blood glucose by periodically testing blood glucose levels. The biological test kit can include a lancet device such as those discussed elsewhere herein. The lancet device can be used to collect a quantity of a biological sample, such as blood from the user. A biological test strip such as glucose strips supported by a strip station can interact with the collected biological sample by electro-chemical or other means. The lancet device and the strip station can be supported by a disposable module. Measuring equipment supported on a reusable module can measure a biological property, such as blood glucose level in milligrams per deciliter. A display monitor supported on the reusable module can display the measured blood glucose level.

A user can repeat this procedure with a second lancet station and a second strip station included on the disposable module of the biological kit. Once the user has used all the lancet stations and all the strip stations on the disposable module of the biological kit, the user can disengage the disposable module by removing the connection between the disposable module connector and the reusable module connector. The reusable module can be retained by the user and another disposable module comprising lancet devices and strip stations can be removably connected to the reusable module using techniques discussed elsewhere herein.

Various examples of the invention have been described. Although the present invention has been described in considerable detail with reference to certain disclosed embodiments, the embodiments are presented for purposes of illustration and not limitation. Other embodiments incorporating the invention are possible. One skilled in the art will appreciate that various changes, adaptations, and modifications may be made without departing from the spirit of the invention and the scope of the appended claims.

The invention claimed is:

1. A biological test kit comprising:
   (a) a reusable module comprising (i) a reusable module housing with top, bottom, front, back, and lateral surfaces, (ii) measuring equipment supported by the reusable module housing and configured to measure a property of a biological sample, and (iii) a reusable module connector supported by at least one of the front, back, or lateral surfaces of the reusable module housing; and
   (b) a disposable module comprising (i) a disposable module housing with top, bottom, front, back, and lateral surfaces, (ii) first and second lancet stations each having a base that is supported by the bottom surface of the disposable module housing and comprising a lancet supported by and stationary with respect to the base and extending toward the top surface of the disposable module housing at an angle of approximately 90° relative to the bottom surface of the disposable module housing, along with a lancet cover that is movable between an un-depressed position in which the lancet cover covers the lancet and a depressed position in which the lancet protrudes through an aperture in the lancet cover, the first lancet station being configured to facilitate generation of a first biological sample, and the second lancet station being configured to facilitate generation of a second biological sample, (iii) first and second strip stations each supported by the disposable module housing, the first strip station and including a first biological strip configured to receive the first biological sample and to provide the first biological sample to the measuring equipment for measurement of the property, and the second strip station including a second biological strip configured to receive the second biological sample and to provide the second biological sample to the measuring equipment for measurement of the property, and (iv) a disposable module connector supported by at least one of the front, back, or lateral surfaces of the disposable module housing and being modularly connectible to the reusable module connector.

2. The biological test kit of claim 1, wherein the disposable module housing comprises (A) a first sub-module housing that supports the first lancet station and includes a first sub-module connector and (B) a second sub-module housing that supports the first strip station and includes a second sub-module connector that is modularly connectible to the first sub-module connector.

3. The biological test kit of claim 1, wherein the disposable module connector and the reusable module connector together comprise an interlocking fastener.

4. The biological test kit of claim 1, wherein the first strip station includes a slot in the disposable module housing and a strip container positioned in the slot, the strip container being configured to slide into and out of the slot between a closed position and an open position and being adapted to provide access to the first biological strip when in the open position.

5. The biological test kit of claim 1, wherein the first strip station comprises:
   a recess defined in the disposable module housing configured to hold the first biological strip, and
   a strip station cover removably connected to the disposable module housing, the strip station cover being configured to cover the recess and prevent access to the first biological strip when in a covered position and to permit access to the first biological strip when in an uncovered position.

6. The biological test kit of claim 1,
   wherein the measuring equipment comprises a correlation mechanism configured to identify a measured biological sample as having originated from the first strip station or the second strip station.

7. The biological test kit of claim 6, wherein the measuring equipment is configured to provide whether the measured biological sample originated from the first strip station or the second strip station to the display monitor for display.

8. The biological test kit of claim 1, wherein the biological test kit has an overall thickness of less than one centimeter.

9. The biological test kit of claim 1, wherein the reusable module further comprises (iv) a display monitor supported by the reusable module housing and configured to display the measured property.

10. The biological test kit of claim 1, wherein the reusable module further comprises (iv) a wireless transmitter supported by the reusable module housing and configured to transmit a signal representative of the measured property to a separate device for display.

11. The biological test kit of claim 1, wherein the reusable module further comprises (iv) a mobile device case connector supported by the reusable module housing and configured to detachably connect the reusable module to a mobile device case.

12. The biological test kit of claim 1, wherein the disposable module further comprises (iv) an insulin delivery device connector supported by the disposable module and configured to detachably connect the disposable module to an insulin delivery device.

13. The biological test kit of claim 1, wherein the biological test kit has a rectangular shape.

* * * * *